United States Patent [19]

Swallow et al.

[11] 4,027,667

[45] June 7, 1977

[54] THERAPEUTIC STOCKING

[75] Inventors: Roger T. Swallow, Crystal Lake, Ill.; John E. Pendergrass, Seneca, S.C.

[73] Assignee: The Kendall Company, Boston, Mass.

[22] Filed: July 3, 1975

[21] Appl. No.: 593,159

[52] U.S. Cl. .................................. 128/165; 2/240; 66/172 E; 66/178 A

[51] Int. Cl.² .................... A61F 13/00; A61F 13/06

[58] Field of Search .......... 128/165, 166, 156, 157; 2/239, 240, 224; 66/172 E, 178 R, 178 A

[56] References Cited

UNITED STATES PATENTS

| | | | |
|---|---|---|---|
| 1,287,870 | 12/1918 | Burk | 128/165 |
| 2,169,203 | 8/1939 | Hinchliff | 66/178 |
| 2,962,885 | 12/1960 | Knohl | 66/178 A |
| 3,362,029 | 1/1968 | Comerma | 2/240 |
| 3,440,665 | 4/1969 | Russell | 2/240 |
| 3,461,695 | 8/1969 | Knohl | 66/178 A |
| 3,856,008 | 12/1974 | Fowler et al. | 128/165 |

Primary Examiner—John D. Yasko
Attorney, Agent, or Firm—Powell L. Sprunger

[57] ABSTRACT

A therapeutic stocking comprising, a circumferentially elastic boot portion having an upper thigh panel for exerting a desired compressive pressure against the upper thigh of a wearer's leg. The upper thigh panel has a limited vertical stretch relative a hip panel for accurate placement of the upper thigh panel on the wearer's upper thigh. The stocking has waist support means, and the hip panel extends between the support means and the upper thigh panel along the side of the wearer's hip. The hip panel is vertically stretchable between the support means and the upper thigh panel to permit placement of the support means on the wearer's waist a variable distance from the upper thigh while the upper thigh panel remains at its proper position on the wearer's upper thigh.

17 Claims, 13 Drawing Figures

U.S. Patent   June 7, 1977   Sheet 1 of 3   4,027,667
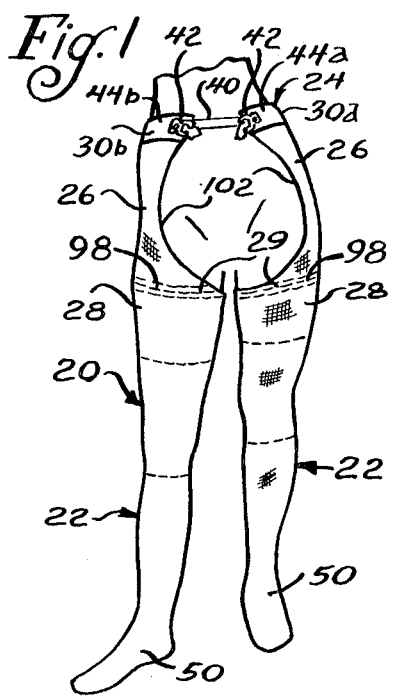
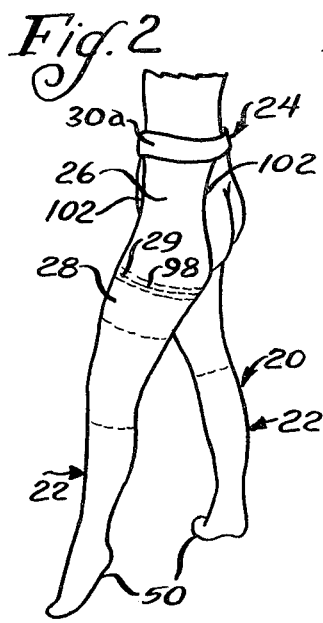
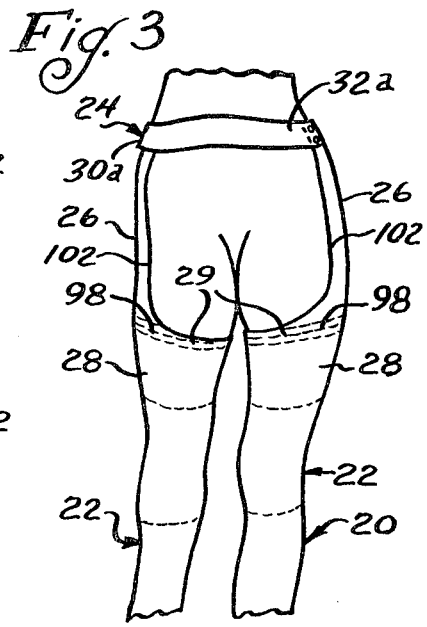
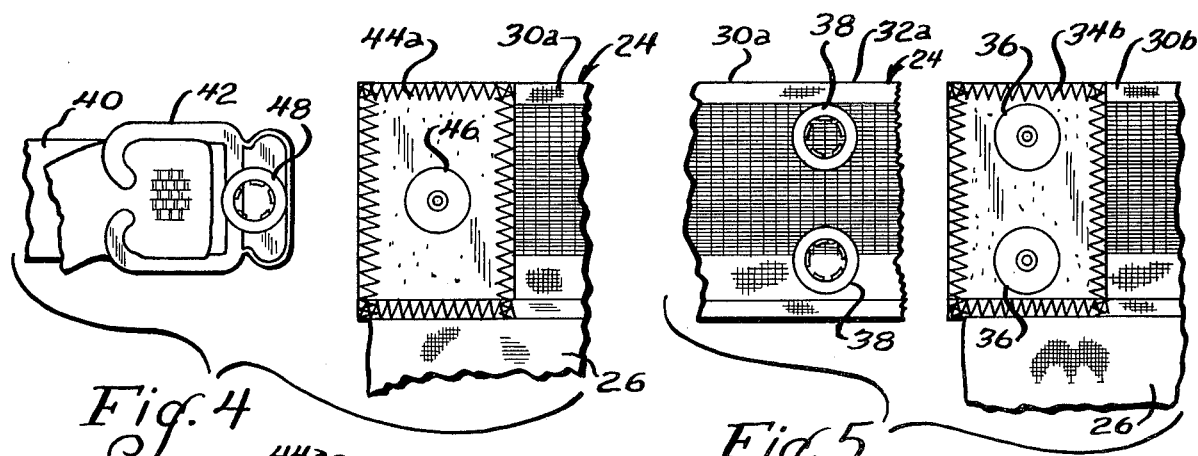
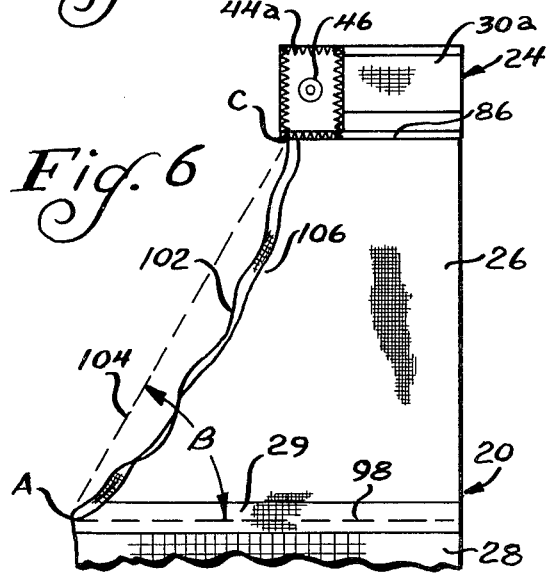
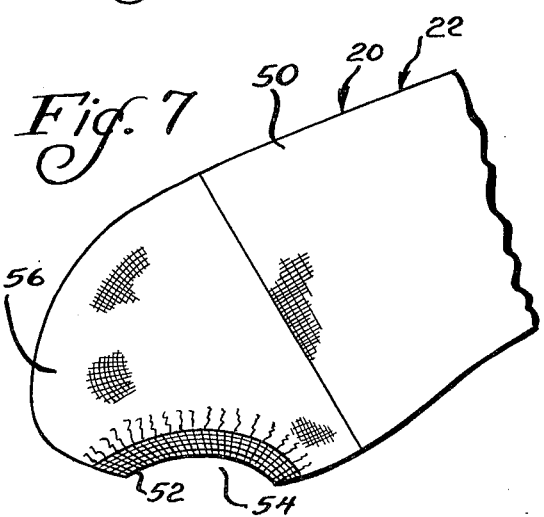

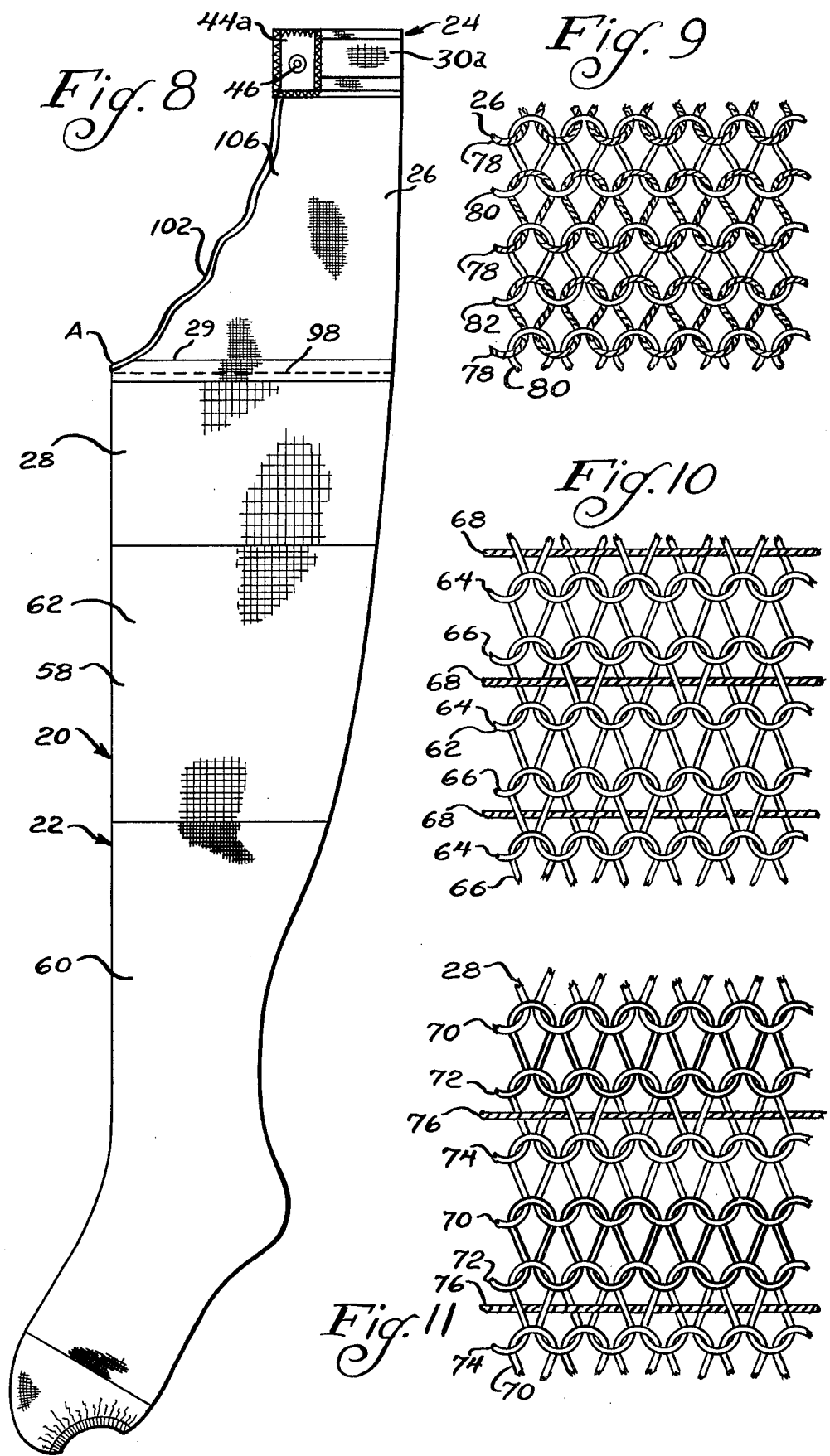

THERAPEUTIC STOCKING

BACKGROUND OF THE INVENTION

The present invention relates to elastic garments, and more particularly to therapeutic stockings.

In the recent past, therapeutic stockings have been prescribed on a relatively wide scale to prevent possible embolism in a patient. When a patient is confined to bed, for example, after an operation, the likelihood of thrombus is markedly increased due to a decrease in the velocity of blood flow in the patient's legs during confinement. Therapeutic or anti-embolism stockings cause application of a compressive pressure against the patient's leg which gradually decreases from the ankle toward the upper part of the leg. Such stockings increase the velocity of blood flow in the legs, and minimize the possiblity of thromboembolism.

Anti-embolism stockings are made in assorted lengths, including those which terminate above the upper thighs of the patient, often termed thigh length stockings. A special difficulty has been encountered in the use of thigh length stockings for oversized patients, e.g., those patient's having a circumference of greater than 25 inches in the region of the upper thigh. Due to the greatly flared configuration of the upper thighs in the legs of such patients, thigh length stockings have a tendency to roll over at their tops, and then slip down the patient's legs. It is undesirable to make the stockings sufficiently tight to prevent such slippage, since the stockings would restrict blood flow through the confined area and would negate the advantages sought by the stocking.

A desirable alternative to thigh length stockings for oversized patients is a stocking which is supported about the patient's waist. Such waist stockings should also exert a compressive pressure against the wearer's leg with a pressure profile generally decreasing from the ankles into the upper thighs, and with the upper thigh portions of the stockings exerting a predetermined pressure in that region of the stocking. Since the stockings extend above the upper thighs of the patient, there is a possibility that the upper thigh portions of the stocking will not be located properly on the patient during placement. Also, due to the varying distances between the waist and the upper thighs of different patients, it may be difficult to properly place the upper thigh portions of a given stocking on an individual patient, or the upper thigh portion of the stocking may become misplaced while the stocking is worn.

The waist supported stocking preferably has openings in the lower abdominal region and for the buttocks to permit post-operative catheterization and wound healing in the perineal region and for bedpan use without removal of the stocking. However, a lower inner side edge of a stocking formed in this manner has a tendency to pull into the inner thighs of the patient, thus limiting passage of blood flow through the femoral vein, particularly if the side edge of the stocking assumes a relatively horizontal position during use. Additionally, such side edges may cause runs in the stockings.

SUMMARY OF THE INVENTION

A principal feature of the present invention is the provision of a waist supported therapeutic stocking which permits proper placement on a patient and which prevents binding of the stocking against the patient's legs during use.

The stocking of the present invention comprises, a circumferentially elastic boot portion having an upper thigh panel for exerting a desired compressive pressure against the upper thigh of the wearer's legs. The stocking has waist support means and a hip panel extending between the support means and the upper thigh panel along the side of the wearer's hip.

A feature of the present invention is the provision of reference means for placement in the gluteal furrow of the patient, in order that the upper thigh panel of the stocking may be accurately placed on the upper thigh of the wearer or patient.

Another feature of the invention is that the upper thigh panel of the stocking has a limited vertical stretch to facilitate accurate placement of the upper thigh panel on the upper thigh of the patient.

Still another feature of the invention is that the hip panel of the stocking has a vertical stretch intermediate the support means and the upper thigh panel of the stocking to permit placement of the support means on the wearer's waist a variable distance from the upper thigh of the patient.

Thus, a feature of the present invention is that the stocking may be placed on patients having a variable range of sizes between their waists and upper thighs while the upper thigh panel of the stocking remains at its proper location on their upper thighs.

Another feature of the invention is that the stocking has an inelastic edging attached along an inner side edge of the stocking hip panel, with the hip panel being prestretched along the side edge prior to attachment of the edging.

Thus, a feature of the invention is that the hip panel of the stocking is permitted to stretch along the inelastic edging during use of the stocking.

Yet another feature of the invention is that the inner side edge of the hip panel has a predetermined angular configuration to prevent lowering and binding of the edging during use of stocking.

Still another feature of the invention is the provision of a run resistant area at the lower end of said side edge to prevent runs in the stocking.

Yet another feature of the invention is that the area may serve as the reference means for placement of the area in the gluteal furrow of the patient.

Further features will become more fully apparent in the following description of the embodiments of this invention and from the appended claims.

DESCRIPTION OF THE DRAWINGS

In the drawings:

FIG. 1 is a front perspective view of a therapeutic stocking of the present invention as worn by a patient;

FIG. 2 is a side perspective view of the stocking of FIG. 1;

FIG. 3 is a fragmentary rear perspective view of the stocking of FIG. 1;

FIG. 4 is a fragmentary plan view of a front fastener for the stocking of FIG. 1;

FIG. 5 is a fragmentary plan view of a rear fastener for the stocking of FIG. 1;

FIG. 6 is a fragmentary plan view of an upper portion of the stocking of FIG. 1;

FIG. 7 is a fragmentary plan view of a toe portion of the stocking of FIG. 1;

FIG. 8 is an elevational view of the stocking of FIG. 1;

FIG. 9 is a typical elastic fabric for a hip panel in the stocking of FIG. 1;

FIG. 10 is a typical elastic fabric for a lower boot portion in the stocking of FIG. 1;

FIG. 11 is a typical elastic fabric for an upper thigh panel in the stocking of FIG. 1;

DESCRIPTION OF THE PREFERRED EMBODIMENTS

Figure 12:
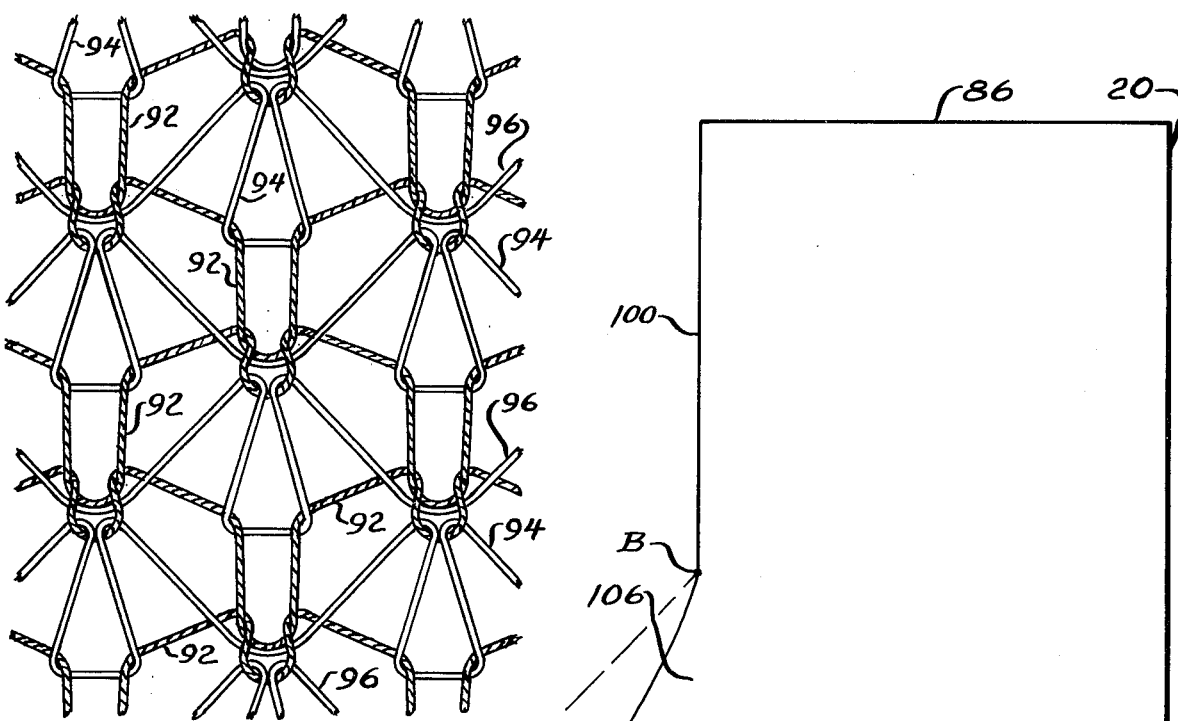
FIG. 12 is a typical elastic fabric for a run resistant area in the stocking of FIG. 1.

Referring now to FIGS. 1–3, there is shown a therapeutic stocking generally designated 20 having a boot portion 22, a waist support means 24, and a pair of hip panels 26 extending along the side of the hips between the waist support means 24 and the boot portion 22. The boot portion 22 exerts a compressive pressure against the patient's legs to increase the velocity of blood flow in the legs, and prevent possible thromboembolism in the patient. In a preferred form, the pressure profile defined by the stocking gradually decreases from the patient's ankles to the upper thighs although the compressive pressure may be reduced somewhat in the area of the knees. The stocking boot portion 22 has a pair of upper thigh panels 28 for exerting a predetermined compressive pressure against the upper thighs of the patient's legs. The stocking 20 also has a pair of run resistant sections or areas 29 which preferably extend circumferentially around the stocking and are located intermediate the upper thigh panels 28 and hip panels 26 for a purpose described below. Although the stocking of the present invention may be utilized on any suitable patient, as desired, the stocking has been found particularly useful for an extra large patient, since the stocking permits accurate placement of the upper thigh panels 28 at their proper location on the patient's legs to define the desired pressure profile without slippage down the leg.

As illustrated in FIGS. 1–5, the support means 24 has a pair of elastic side bands 30a and 30b secured by suitable means, such as an overedge stitch, to the respective upper ends of the hip panels 26. As shown, the band 30a extends around the back of the patient, and one end 32a of the band 30a is releasably attached to one end 34b of the band 30b by suitable means, such as a pair of male and female snap fasteners 36 and 38, respectively. As shown in FIGS. 1 and 4, the stocking 20 also has an elastic or inelastic front band 40, as desired, which may have a smaller width than the side bands 30a and b. The opposed ends of the front band 40 are slidably received in a pair of fastening elements 42 to permit adjustment of the band 40 between the other ends 44a and 44b, respectively, of the side bands 30a and b. The opposed ends of the front band 40 may be releasably attached by the fastening elements 42 to the ends 44a and b of the side bands 30a and b by suitable means, such as male and female snap fasteners 46 and 48, as shown. Thus, the circumference of the waist support means 24 may be modified to the particular waist size of a patient by adjusting the front band 40 in the fastening elements 42, and the front band 40 may be completely removed from a used stocking for purposes of laundering, if desired. Also, the stocking may include another set of fasteners for removal of the back portion of the band 30a from the stocking.

As shown in FIG. 7, the foot portion 50 may have an edging 52, such as welt, which defines a toe inspection opening 54 which underlies the toes when the stocking is worn. Accordingly, an outer toe portion 56 of the stocking may be pulled over the toes to inspect the toes through the opening 54 without removal of the stocking from the patient.

Referring to FIG. 8, the stocking 20 may be formed as follows. The lower boot portion 58 is preferably made of a circumferentially elastic fabric having a limited vertical stretch, and may have a calf panel 60, and a knee panel 62 which extends between the calf panel 60 and the upper thigh panel 28, with the calf panel 60 exerting a greater compressive pressure against the wearer's leg than the knee panel 62. A lower thigh panel may be included between the knee panel and the upper thigh panel, if desired. As shown in FIG. 10, the panel 62, as well as the panel 60, may have alternating courses of jersey knit stitches of non-elastomeric yarns 64 and 66. The yarns 64 are preferably of Z-twist stretch nylon, such as 70/1, 17 filament Z-twist nylon 66 yarn, while the yarns 66 are preferably of S-twist stretch nylon, such as 70/1, 17 filament S-twist nylon 66 yarn. A covered elastomeric yarn 68, such as a single covered elastomeric yarn having a 280 denier spandex core and a covering of 70/1, 34 filament nylon 6 yarn, is preferably inlaid into every other course of the jersey stitches. The elastomeric yarns may be inlaid into either course of S-twist or Z-twist yarns, as desired. If desired, the elastomeric yarns 68 may be inlaid in every course of the jersey stitches in the calf panels 60 to provide a greater compressive pressure against the lower part of the legs.

Referring to FIG. 11, the upper thigh panels 28 preferably have contiguous courses of jersey knit stitches of non-elastomeric yarns 70, 72, and 74. The yarns 74 are preferably of Z-twist nylon, such as 70/1, 17 filament Z-twist nylon 66 yarn, while the yarns 70 are preferably of S-twist nylon, such as 70/1, 17 filament S-twist nylon 66 yarn. The courses of the yarns 72 are intermediate the courses of S and Z-twist yarns 70 and 74, respectively, and the yarns 72 are preferably of a balanced yarn, such as 40/2, 13 filament semi-dull stretch nylon 66 yarn. A covered elastomeric yarn 76, such as a single covered elastomeric yarn having a 280 denier spandex core and a covering of 70/1, 34filament nylon 6 yarn, is inlaid into the courses of Z-twist yarns 74, or S-twist yarns 70, as desired. Accordingly, the elastomeric yarns 76 are inlaid in every third course of the thigh panels 28, and intermediate the courses of S-twist yarns 70 and balanced yarns 72. The structure of the thigh panel 78 permits enlargement of the frame during knitting to provide the critical reduced compressive pressures in the upper thigh regions of the patient, and provides a limited vertical stretch in the panels for a purpose which will be described below.

The hip panels 26 are preferably made of a two-way stretch fabric. As shown in FIG. 9, the hip panels 26 have alternating courses of jersey knit stitches of a covered elastomeric yarn 78, such as a 70 denier spandex core double-covered with 20/6 nylon 6 covering yarns. The hip panels 26 have alternating courses of a non-elastomeric yarn, with a first course of preferably an S-twist yarn 80, such as a 70/1, 17 filament S-twist nylon 66 yarn, and a second course of Z-twist yarn 82, such as a 70/1, 17 filament Z-twist nylon 66 yarn. Thus, the S and Z-twist yarns 80 and 82, respectively, are formed in every fourth course of the hip panels 26. The fabric of the hip panels provides a circumferential and vertical stretch for a purpose which will be described below.

As shown in FIG. 12, the sections 29 of run resistant fabric have courses of stitches of a covered elastomeric yarn 92, such as a 70 denier spandex core double-covered with 20/6 nylon 6 covering yarns. Alternate rounds of the yarns 92 have jersey knit stitches, and alternate rounds are separated by non-elastomeric yarns 94 and 96 in different courses. As shown, the contiguous knits of yarns 92 are separated in every other round by knits of the yarns 94 and 96 in different courses, thus defining an alternate knit and tuck structure of the non-elastomeric yarns 94 and 96, and a straight knit of the elastomeric yarns 92, with the section 29 having a two-way stretch. Alternatively, elastomeric yarns may have an alternate knit and tuck structure, while the non-elastomeric yarns have a straight knit. The yarns 94 may be of S-twist nylon, such as 70/1, 17 filament S-twist nylon 66 yarn, while the yarns 96 may be of Z-twist nylon, such as 70/1, 17 filament Z-twist nylon 66 yarn. The run resistant section is adapted to prevent binding against the wearer for variable leg circumferences encountered.

Figure 13:
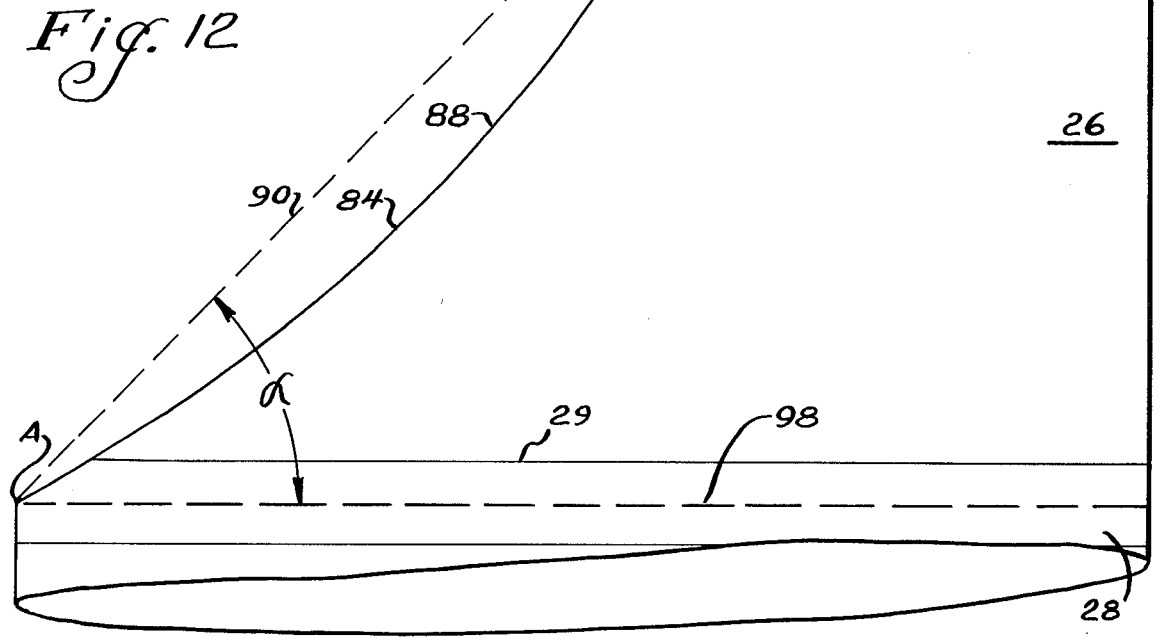
FIG. 13 is a fragmentary plan view of an upper portion of the stocking during formation.

As shown in FIG. 13, after the stocking blanks have been knitted and boarded, the blanks may be cut for convenience to define an inner side edge 84 of the hip panels 26 extending from a lower point A of the side edges 84 to an upper edge 86 of the hip panels 26. The side edges 84 have a lower arcuate portion 88 which extends from point A to a point B which is spaced below the upper edge 86 of the stocking. A line 90 drawn through points A and B defines an acute angle alpha relative an imaginary line 98 which extends laterally through the stocking from point A, and which is preferably located in the section 29. Thus, the end points A and B of the lower arcuate edge 88 define the angle alpha relative the lateral line 98, and in a preferred form the angle alpha is in the range of 35°to 55 °and preferably greater than or equal to 45°,for a purpose which will be described below. As shown, the side edges 84 also have an upper vertically extending portion 100, which is generally perpendicular to the reference line 98, and which extends between the point B at the juncture of edges 88 and 100, and between the upper edges 86 of the hip panels 26.

As shown in the drawings, the lower end of the side edge 84 adjacent point A is preferably located in the section 29, or immediately above the section 29. Thus, the section 29 of run resistant material resists propogation of runs through the section toward the upper thigh panels 28, which otherwise might occur if the lower end of the side edge 84 terminated in these panels without use of the section 29.

As shown in FIGS. 6 and 8, an inelastic edging 102 is attached along the inner side edges 84 of the hip panels 26 to provide a comfortable inner side edge of the hip panels and prevent elastomers in the hip panels from pulling out of the edging 102. The edging 102 also minimizes the formation of runs in the hip panels. The edging 102 may be of any suitable type, such as a Mauser stitch or edging, known to the art as stitch type 607, as defined by Federal Standard No. 751a, Jan. 25, 1965, entitled "Stitches, Seams, and Stitching". The hip panels 26 are prestretched along their inner side edges 84 before the edging 102 is formed along the side edges. After the formation of the edgings 104 on the pre-stretched fabric, the sides of the hip panels 26 are released and the edgings form a puckered configuration of the hip panels along the edgings, and an arcuate inner edge of the hip panels. As shown in FIG. 6, a reference line 104 drawn through point A and a point C at the intersection of the edging 102 and the upper edge 86 defines an acute angle beta between the line 104 and the reference line 98. Although the edging 102 itself is inelastic and is not permitted to expand, the side margins 106 of the hip panels 26 along the edging 102 is permitted to expand during use of the stocking, since the edging 102 was attached with the side margins of the hip panels being prestretched. Thus, the edgings 102 and the side margins 106 of the hip panels 26 limit binding of the stocking against the patient's inner thigh for variable leg circumferences at the lower end of the edgings 102 adjacent point A. When the stocking 20 is placed on a patient, the lower boot portion and the thigh panels 26 are twisted slightly to position the inner side edging 102 approximately 90°relative the foot portion of the stocking, as best shown in FIGS. 1–3.

During placement of the stocking, the upper thigh panels 28 should be accurately placed on the upper thighs of the patient to define the desired pressure profile in the patient's upper thighs, as well as the regions of the legs below the upper thighs. In a preferred form, reference means is provided for placement of the upper end of the upper thigh panels 28 adjacent the gluteal furrow of the patient, such that the upper thigh panels 28 extend downwardly in a correct position from the reference means and the gluteal furrow once the stocking has been properly placed. In a preferred form, the area 29 defines the desired reference position of the stocking for the gluteal furrow. Hence, the visibly recognizable area 29 may be readily positioned in the gluteal furrow, such that the upper thigh panels 28 are properly positioned on the patient's upper thighs for use. In a preferred embodiment, the reference line 98 defines the proper stocking location for the gluteal furrow; and, accordingly, the line 98 would normally be located in the region of the section 29.

Of course, it is important that the upper thigh panels 28 do not become misplaced from the upper thighs during use of the stocking. Accordingly, the hip panels 26 have a vertical stretch to permit flexation of the hip panels as the support means 24 is positioned about the waist of the patient. Thus, the upper thigh panels 28 remain at their proper position when the stockings have been placed on the patient, since the hip panels 26 may assume a modified length depending on the distance between the waist and upper thigh of an individual patient, which will vary from patient to patient. In this manner, the upper thigh panels may be properly located on the patient during placement of the stocking to define the desired compressive pressure profile from the patient's ankles through the upper thighs, and once placed the upper thigh panels remain at their proper position during use of the stocking.

It will be recalled in connection with FIG. 13 that the reference lines 90 and 98 define an angle alpha which is preferably greater than 35°and less than 55°.It has been found that if the reference angle alpha is too small, the edging 102 will assume a generally horizontal configuration about the patient's leg during use of the stocking, and particularly when the stocking is worn by an oversized patient. In this configuration, the lower inner portion of the edging 102 adjacent point A cuts into or binds against the inner thighs of the patient's legs, particularly since tension is applied to the stockings by the waist support means 24 through the hip panels 26, and thus restricts the flow of blood through the femoral veins. It has been determined that by making the included angle alpha greater than 35°, and preferably greater than 45°, the edging 102 of the hip panels 26 will remain in a generally arcuate configuration extending from the crotch region of the patient to his waist during use of the stocking, as directed. However, if the reference angle alpha is greater than 55°, the inner side margins of the hip panels 26 will cover the lower abdominal portion of the patient, and will obstruct catheterization or will prevent wound healing in this area. Similarly, it is desirable that the back portion of the edging 102 in the hip panels passes around the sides of the buttocks between the patient's crotch and waist for comfort of the wearer and to permit bedpan use without removal of the stocking.

The foregoing detailed description is given for clearness of understanding only, and no unnecessary limitations should be understood therefrom, as modifications will be obvious to those skilled in the art.

What is claimed is:

1. A therapeutic stocking, comprising: a circumferentially elastic boot portion having an upper thigh panel for exerting a desired compressive pressure against the upper thigh of a wearer's leg, said upper thigh panel having a limited vertical stretch for accurate placement of the upper thigh panel on the wearer's upper thigh, waist support means, and a hip panel extending between the support means and said upper thigh panel along the side of the wearer's hip, said hip panel being vertically stretchable between the support means and upper thigh panel to permit placement of the support means on the wearer's waist a variable distance from the upper thigh while the upper thigh panel remains at its proper position on the wearer's upper thigh.

2. The stocking of claim 1 wherein said upper thigh panel comprises courses of jersey knit stitches of non-elastomeric yarn, and an elastomeric yarn inlaid into every third course of said stitches.

3. The stocking of claim 2 wherein the courses of non-elastomeric yarn comprises, contiguous courses of a Z-twist yarn, an S-twist yarn, and a balanced yarn.

4. The stocking of claim 3 wherein said elastomeric yarns are inlaid in the Z-twist yarn intermediate courses of said balanced and S-twist yarns.

5. The stocking of claim 2 wherein the boot portion below said upper thigh panel comprises, courses of jersey knit stitches of non-elastomeric yarn, and an elastomeric yarn inlaid into less than every third course of said stitches.

6. The stocking of claim 1 wherein said hip panel comprises, courses of jersey knit stitches of non-elastomeric yarn alternating with courses of jersey knit stitches of elastomeric yarn.

7. The stocking of claim 1 including a run-resistant area intermediate said upper thigh and hip panels.

8. The stocking of claim 7 wherein said area comprises an alternating knit tuck of non-elastomeric yarns, and a straight knit of elastomeric yarns.

9. A therapeutic stocking, comprising: a circumferentially elastic boot portion having an upper thigh panel for exerting a desired compressive pressure againt the upper thigh of a wearer's leg, waist support means, a hip panel extending between the support means and said upper thigh panel along the side of the wearer's hip, said hip panel having an edge extending between the crotch region of the wearer and the support means, with the hip panel being stretchable along said edge, and an inelastic edging secured to the hip panel along said edge, with the hip panel being prestretched along the edge prior to attachment of said edging.

10. The stocking of claim 9 wherein said hip panel comprises a two-way stretch knitted fabric.

11. The stocking of claim 9 including a region of run-resistant material intermediate the upper thigh and hip panels at the lower end of said edge.

12. A therapeutic stocking, comprising: a circumferentially elastic boot portion having an upper thigh panel for exerting a desired compressive pressure against the upper thight of a wearer's leg, a hip panel extending longitudinally above the thigh panel toward an upper edge of the stocking adjacent the wearer's waist, said hip panel having a side edge defining a cutout for the wearer's lower abdomen and buttocks, said hip panel having a first lower section defining an arcuate configuration of said side edge, and a second upper section extending between the first section and said upper edge and defining an extension of the side edge intermediate the arcuate edge and said upper edge, with a line drawn between a first point at the lower end of the arcuate edge and a second point at the juncture of the side edges in said first and second sections defining a predetermined angle relative a line extending through said first point and laterally through the stocking, said angle being in the range of 35 to 55 degrees, said hip panel being stretchable along said side edge, and including an inelastic edging secured to the stocking along said side edge, said hip panel being prestretched along said side edge prior to attachment of said edging to the hip panel, whereby the attached edging generally defines an arcuate edge of the hip panel extending from said first point to said upper edge.

13. The stocking of claim 12 wherein said angle is greater than or equal to 45°.

14. The stocking of claim 12 wherein the side edge of said second section defines a line extending generally perpendicular to said lateral line.

15. The stocking of claim 12 including a run-resistant area, with said lateral line extending through said area.

16. A therapeutic stocking, comprising: a circumferentially elastic boot portion having an upper thigh panel of limited vertical stretch for exerting a desired compressive pressure against the upper thigh of a wearer's leg, waist support means, a hip panel extending between said support means and said upper thigh panel, a side edge extending downwardly from said support means, and visible reference means adjacent the upper end of said upper thigh panel to indicate the location for placement of the stocking in the gluteal furrow of the wearer, said reference means comprising a relatively narrow run-resistant section extending at least partially circumferentially around the stocking at the lower end of said side edge and having upper and lower edges defining a visibly recognizable region intermediate said upper thigh and hip panels, said upper thigh panel extending downwardly from said reference means to cover the upper thigh panel extending downwardly from said reference means to cover the upper thigh of the wearer.

17. The stocking of claim 16 in which said hip panel comprises a knitted fabric having a two-way stretch.

* * * * *